US012691155B2

(12) United States Patent
Xiao et al.

(10) Patent No.: US 12,691,155 B2
(45) Date of Patent: Jul. 28, 2026

(54) TRADITIONAL CHINESE MEDICINE COMPOSITION, AND PREPARATION METHOD THEREFOR AND USE THEREOF

(71) Applicant: JIANGSU KANION PHARMACEUTICAL CO., LTD., Lianyungang (CN)

(72) Inventors: Wei Xiao, Lianyungang (CN); Wenjun Liu, Lianyungang (CN); Ziyan Dong, Lianyungang (CN); Shasha Gu, Lianyungang (CN); Chenfeng Zhang, Lianyungang (CN); Tuanjie Wang, Lianyungang (CN); Liang Cao, Lianyungang (CN); Zhenzhong Wang, Lianyungang (CN)

(73) Assignee: JIANGSU KANION PHARMACEUTICAL CO., Lianyungang (CN)

( * ) Notice: Subject to any disclaimer, the term of this patent is extended or adjusted under 35 U.S.C. 154(b) by 31 days.

(21) Appl. No.: 18/856,744

(22) PCT Filed: Feb. 6, 2023

(86) PCT No.: PCT/CN2023/074582
§ 371 (c)(1),
(2) Date: Oct. 14, 2024

(87) PCT Pub. No.: WO2023/197731
PCT Pub. Date: Oct. 19, 2023

(65) Prior Publication Data
US 2025/0241975 A1 Jul. 31, 2025

(30) Foreign Application Priority Data
Apr. 13, 2022 (CN) ......................... 202210382202.1

(51) Int. Cl.
| | |
|---|---|
| *A61K 36/736* | (2006.01) |
| *A61K 31/12* | (2006.01) |
| *A61K 31/192* | (2006.01) |
| *A61K 31/216* | (2006.01) |
| *A61K 31/7028* | (2006.01) |
| *A61K 31/7048* | (2006.01) |
| *A61K 36/076* | (2006.01) |
| *A61K 36/54* | (2006.01) |
| *A61K 36/65* | (2006.01) |
| *A61P 15/00* | (2006.01) |

(52) U.S. Cl.
CPC ............ *A61K 36/736* (2013.01); *A61K 31/12* (2013.01); *A61K 31/192* (2013.01); *A61K 31/216* (2013.01); *A61K 31/7028* (2013.01); *A61K 31/7048* (2013.01); *A61K 36/076* (2013.01); *A61K 36/54* (2013.01); *A61K 36/65* (2013.01); *A61P 15/00* (2018.01); *A61K 2236/331* (2013.01); *A61K 2236/333* (2013.01); *A61K 2236/39* (2013.01); *A61K 2236/51* (2013.01); *A61K 2236/53* (2013.01)

(58) Field of Classification Search
CPC .... A61K 36/736; A61K 31/12; A61K 31/192; A61K 31/216; A61K 31/7028; A61K 31/7048; A61K 36/076; A61K 36/54; A61K 36/65; A61K 2236/331; A61K 2236/333; A61K 2236/39; A61K 2236/51; A61K 2236/53; A61K 31/352; A61K 36/71; A61P 15/00; A61P 29/00
See application file for complete search history.

(56) References Cited

U.S. PATENT DOCUMENTS

2017/0080043 A1* 3/2017 Zhou .................... A61K 36/718

FOREIGN PATENT DOCUMENTS

| | | |
|---|---|---|
| CN | 1660149 A | 8/2005 |
| CN | 1209124 C | 2/2006 |
| CN | 1733104 A | 2/2006 |
| CN | 1927288 A | 3/2007 |
| CN | 1843424 A | 7/2009 |
| CN | 106153803 A | 11/2016 |
| DE | 112014006651 T5 * | 2/2017 ................ A61P 3/06 |

OTHER PUBLICATIONS

Zhou J, machine translation of DE-112014006651-T5, 14 pages (Year: 2017).*

丁玥 等 (Ding, Yue et al.). "桂枝茯苓胶囊质量标准提升对制剂主要药效影响的研究 (Monitor on Influence of Quality Standard Improvement upon Guizhi Fuling Capsules Efficacy)" 中国中药杂志 (China Journal of Chinese Materia Medica), vol. 40, No. (19), Oct. 1, 2015 (Oct. 1, 2015), p. 3792.

杨慧敏 等 (Yang, Huimin et al.). "基于 UPLC-ESI-Q-TOF-MS/MS 技术的桂枝茯苓胶囊化学成分分析 (Identification of Chemical Constituents in Guizhi Fuling Capsules by UPLC-Q-TOF-MS/MS)" 中国中药杂志 (China Journal of Chinese Materia Medica), vol. 45, No. (04), Feb. 28, 2020 (Feb. 28, 2020), p. 861 abstract, pp. 863-871 table 1.

陶晓倩 等 (Tao, Xiaoqian et al.). "桂枝茯苓胶囊中三要成分对人子宫肌瘤细胞增殖及小

(Continued)

*Primary Examiner* — Aaron J Kosar
(74) *Attorney, Agent, or Firm* — Adam Warwick Bell; Matthew Rupert Kaser

(57) ABSTRACT

Provided are a traditional Chinese medicine composition, a preparation method therefor, and use thereof, the following in percentage by mass: 0.214% or above of gallic acid, 0.008% or above of 4-hydroxybenzoic acid, 0.083% or above of oxypaeoniflorin, 1.112% or above of paeoniflorin, 0.010% or above of ethyl gallate, 0.155% or above of 1,2,3,4,6-O-pentagalloylglucose, 0.041% or above of benzoic acid, 0.015% or above of cinnamic acid, 0.093% or above of benzoyl paeoniflorin, 0.037% or The traditional Chinese medicine composition can alleviate dysmenorrhea.

8 Claims, 3 Drawing Sheets

(56)           References Cited

OTHER PUBLICATIONS

鼠离体子宫收缩活动的影响 (Effect of Main Components from Guizhi Fuling Capsule on Human Leiomyoma Cell Proliferation and Contraction of Isolated Mouse Uterine)" 中国实验方剂学杂志 (Chinese Journal of Experimental Traditional Medical Formulae), vol. 22, No. (02), Jan. 20, 2016 (Jan. 20, 2016), p. 91 abstract, p. 95 table 3.

* cited by examiner

TRADITIONAL CHINESE MEDICINE COMPOSITION, AND PREPARATION METHOD THEREFOR AND USE THEREOF

BACKGROUND OF THE INVENTION

1. Technical Field

The present invention relates to the technical field of traditional Chinese medicine, particularly to a traditional Chinese medicine composition, its preparation method, and use thereof.

2. Description of Related Art

The prescription of Guizhi Fuling Capsules originates from the classic formula Guizhi Fuling Wan by Zhang Zhongjing, a famous physician from the Han Dynasty, as documented in the 'Jin Gui Yao Lue'. It consists of five Chinese medicinal ingredients: Guizhi (*Cinnamomi ramulus*), Fuling (*Poria cocos*), Mudan Pi (*Moutan cortex*), Thoren (*Persicae semen*), and Baishao (*Radix paeoniae alba*). This combination has effects such as promoting blood circulation, resolving blood stasis, and eliminating congestion and swelling. It is used for conditions caused by blood stasis obstructing the vessels in women, including masses due to stasis, amenorrhea, dysmenorrhea, and incomplete lochia after childbirth; uterine fibroids, chronic pelvic inflammatory masses, dysmenorrhea, endometriosis, and ovarian cysts with the above symptoms. It can also be used for breast hyperplasia classified under the category of blood stasis obstructing the breasts, presenting with breast pain, breast masses, and chest discomfort; or for benign prostatic hyperplasia classified under the category of blood stasis obstructing the bladder, presenting with discomfort in urination, thin urine stream, dribbling urine, and lower abdominal distension and pain.

Patent Application No.: 200310116836.X discloses the application of a Guizhi Fuling combination in treating benign prostatic hyperplasia and breast diseases. The formula is composed of Guizhi, Fuling, Mudan Pi, Taoren, and Baishao in specific proportions. Trials have shown that the aforementioned compound combination exhibits good efficacy in treating benign prostatic hyperplasia and breast hyperplasia.

However, for traditional Chinese medicine compounds, the effective ingredients in complex systems are not clearly defined. The significant impact of which main ingredients affect efficacy and the reasonable optimal content range need to be reasonably controlled for different effective ingredients. Moreover, since most of the raw materials originate from natural products and are influenced by factors such as origin, growth period, harvesting season, and cultivation and processing techniques, the quality of medicinal materials varies greatly. Even if the medicinal materials meet the requirements of pharmacopoeia standards, different batches of raw materials from different origins can lead to instability in the composition of preparations and poor consistency in quality. It can be seen that a prescription based solely on the weight of medicinal materials cannot meet the production requirements of modern traditional Chinese medicine, severely restricting the stability and controllability of clinical efficacy of traditional Chinese medicine and the reproducibility and acceptance of modern research results.

BRIEF SUMMARY OF THE INVENTION

The present invention aims to further study a traditional Chinese medicine compound composed of five medicinal ingredients: *Cinnamomi Ramulus, Poria cocos, Moutan cortex, Persicae semen*, and *Paeoniae radix alba*. This involves analyzing the composition and medicinal effects of the medicine compound through the combination of herbs from different sources and batches, focusing on the relationship between major components exhibiting significant content variations within the compound and their medicinal effects, to identify specific active ingredients and their appropriate concentrations that impact efficacy, thereby selecting traditional Chinese medicine compound with enhanced activity to ensure stable quality and reliable therapeutic effects of traditional Chinese medicine products.

In view of this, the present invention proposes a medicinal composition characterized by active ingredients derived from *Cinnamomi ramulus, Poria cocos, Moutan cortex, Persicae semen*, and *Paeoniae radix alba*, quantified in mass percentages, the active ingredients comprise: gallic acid approximately 0.214% or more, p-hydroxybenzoic acid approximately 0.008% or more, oxidized paeoniflorin approximately 0.083% or more, paeoniflorin approximately 1.112% or more, ethyl gallate approximately 0.010% or more, 1,2,3,4,6-O-pent-galloylglucose approximately 0.155% or more, benzoic acid approximately 0.041% or more, cinnamic acid approximately 0.015% or more, benzoylpaeoniflorin approximately 0.093% or more, cinnamaldehyde approximately 0.037% or more, paeonol approximately 0.622% or more, amygdalin approximately 1.001% or more, water-soluble polysaccharides approximately 1.743% or more, alkali-soluble polysaccharides approximately 29.671% or more, total monosaccharides and disaccharides approximately 9.231% or more.

Preferably, gallic acid 0.433-0.740%, p-hydroxybenzoic acid 0.011-0.054%, oxidized paeoniflorin 0.097-0.201%, paeoniflorin 1.235-1.991%, ethyl gallate 0.012-0.094%, 1,2,3,4,6-O-penta-galloylglucose 0.294-0.702%, benzoic acid 0.045-0.135%, cinnamic acid 0.021-0.062%, benzoylpaeoniflorin 0.101-0.236%, cinnamaldehyde 0.045-0.511%, paeonol 0.728-1.202%, amygdalin 1.114-1.492%, water-soluble polysaccharides 1.851-3.702%, alkali-soluble polysaccharides 30.198-40.206%, monosaccharides and disaccharides 9.966-15.438%.

According to another embodiment of the present invention, active ingredients derived from *Cinnamomi ramuhus, Poria cocos, Moutan cortex, Persicae semen*, and *Paeoniae radix alba*, characterized by the following proportional ranges of active ingredients: gallic acid 0.433-0.740, p-hydroxybenzoic acid 0.011-0.054, oxidized paeoniflorin 0.097-0.201, paeoniflorin 1.235-1.991, ethyl gallate 0.012-0.094, 1,2,3,4,6-O-penta-galloylglucose 0.294-0.702, benzoic acid 0.045-0.135, cinnamic acid 0.021-0.062, benzoylpaeoniflorin 0.101-0.236, cinnamaldehyde 0.045-0.511, paeonol 0.728-1.202, amygdalin 1.114-1.492, water-soluble polysaccharides 1.851-3.702, alkali-soluble polysaccharides 30.198-40.206, monosaccharides and disaccharides 9.966-15.438.

Specifically, the medicinal composition can be formulated into any suitable dosage form, including but not limited to extracts, tablets, capsules, pills, powders, granules, and pellets.

Optionally, the preparation method of the traditional Chinese medicine composition comprises: weighing raw medicinal materials including *Cinnamomi ramulus, Poria cocos, Moutan cortex, Persicae semen*, and *Paeoniae radix alba* in a 1:1:1:1:1 ratio by weight; 80% of the prescribed amount of *Poria cocos* is powdered; *Moutan cortex* is steam-distilled with water vapor to collect the distillate, from which volatile components are separated and set aside;

the residue, along with *Cinnamomi ramulus, Paeoniae radix alba, Persicae semen* and the remaining 20% of *Poria cocos*, undergoes dual extraction with 90% ethanol, the extracts are combined, ethanol is completely removed by evaporation, and the residue is further extracted twice with water, the filtrates combined, concentrated under reduced pressure, and mixed with finely powdered *Poria cocos* and the volatile components of *Moutan cortex.*

Optionally, the preparation method of the traditional Chinese medicine composition comprises: weighing raw medicinal materials including *Cinnamomi ramulus, Poria cocos, Moutan cortex, Persicae semen*, and *Paeoniae radix alba* in a 1:1:1:1:1 ratio by weight; grinding *Cinnamomi ramulus, Persicae semen, Paeoniae radix alba, Moutan cortex*, and half of the prescribed amount of *Poria cocos* into coarse powder, mixing uniformly, adding 90% ethanol at 3 times the amount of medicinal materials, soaking for 0.5 hours, refluxing for 1 hour, and filtering; refluxing the residue with 90% ethanol at 3 times the amount of raw medicinal materials, filtering, and combining the filtrates; refluxing the residue with 5 times the amount of water for 0.5 h, filtering; refluxing the residue with 5 times the amount of water for 0.5 h, filtering; combining the filtrates and discarding the residue; concentrating the ethanol extract and water extract separately under reduced pressure, recovering the ethanol extract until no alcohol odor remains; combining the two concentrated solutions to obtain a brown paste; mixing remaining 50% of the prescribed amount of finely powdered *Poria cocos* with the above paste, drying, and pulverizing to obtain a dry paste powder, and adding excipients.

Use of a traditional Chinese medicine composition according to any one of claims 1-3 in the manufacturing of a drug for improving dysmenorrhea.

The "use" refers to administering the extracts to subjects with corresponding diseases or tendencies towards such diseases, aiming to achieve therapeutic effects such as curing, alleviating, altering, affecting, improving, or preventing the diseases, symptoms, or tendencies mentioned. Those skilled in the art can determine specific effective doses easily based on the type of disease being treated, route of administration, and use of excipients, which may vary due to concurrent use of other drugs.

The present invention has been validated using a rodent model, confirming that the aforementioned extracts significantly improve symptoms of primary dysmenorrhea and other related menstrual disorders.

The above ingredient content ratios also provide the basis for quality control of the Chinese medicine composition, namely, the present invention proposes a method for quality control of the aforementioned Chinese medicine composition, characterized in that, among the active ingredients: gallic acid approximately 0.214% or more, p-hydroxybenzoic acid approximately 0.008% or more, oxidized paeoniflorin approximately 0.083% or more, paeoniflorin approximately 1.112% or more, ethyl gallate approximately 0.010% or more, 1,2,3,4,6-O-pent-galloylglucose approximately 0.155% or more, benzoic acid approximately 0.041% or more, cinnamic acid approximately 0.015% or more, benzoylpaeoniflorin approximately 0.093% or more, cinnamaldehyde approximately 0.037% or more, paeonol approximately 0.622% or more, amygdalin approximately 1.001% or more, water-soluble polysaccharides approximately 1.743% or more, alkali-soluble polysaccharides approximately 29.671% or more, total monosaccharides and disaccharides approximately 9.231% or more.

Furthermore, the proportional relationships of the above active ingredients are: gallic acid 0.433-0.740, p-hydroxybenzoic acid 0.011-0.054, oxidized paeoniflorin 0.097-0.201, paeoniflorin 1.235-1.991, ethyl gallate 0.012-0.094, 1,2,3,4,6-O-penta-galloylglucose 0.294-0.702, benzoic acid 0.045-0.135, cinnamic acid 0.021-0.062, benzoylpaeoniflorin 0.101-0.236, cinnamaldehyde 0.045-0.511, paeonol 0.728-1.202, amygdalin 1.114-1.492, water-soluble polysaccharides 1.851-3.702, alkali-soluble polysaccharides 30.198-40.206, monosaccharides and disaccharides 9.966-15.438.

Moreover, the chromatographic profiles of *Cinnamomi ramulus, Poria cocos, Moutan cortex, Persicae semen*, and *Paeoniae radix alba* used in the above Chinese medicine composition fall within the data ranges of Tables 5 to 9, or compared individually with Tables 5 to 9, with a similarity not less than 0.90, preferably 0.95.

The present invention demonstrates through studies on the effects of active ingredients of the Chinese medicine composition on mouse writhing and serum estradiol (E2) and progesterone (P) levels that the Chinese medicine composition with specific active ingredient content characteristics has better therapeutic effects for chronic pelvic inflammation, endometriosis, and dysmenorrhea. The aforementioned active ingredient content characteristics can be used for quality control of the Chinese medicine composition.

DETAILED DESCRIPTION OF THE INVENTION

Figure 1:
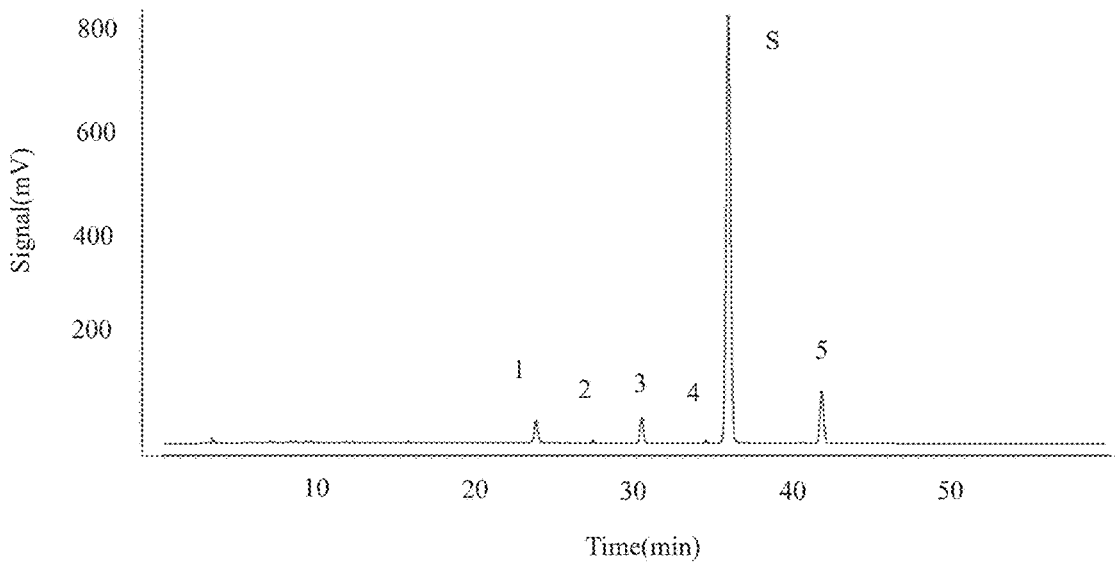
FIG. 1 shows the fingerprint chromatogram of *Ramulus Cinnamomi;*
Figure 2:
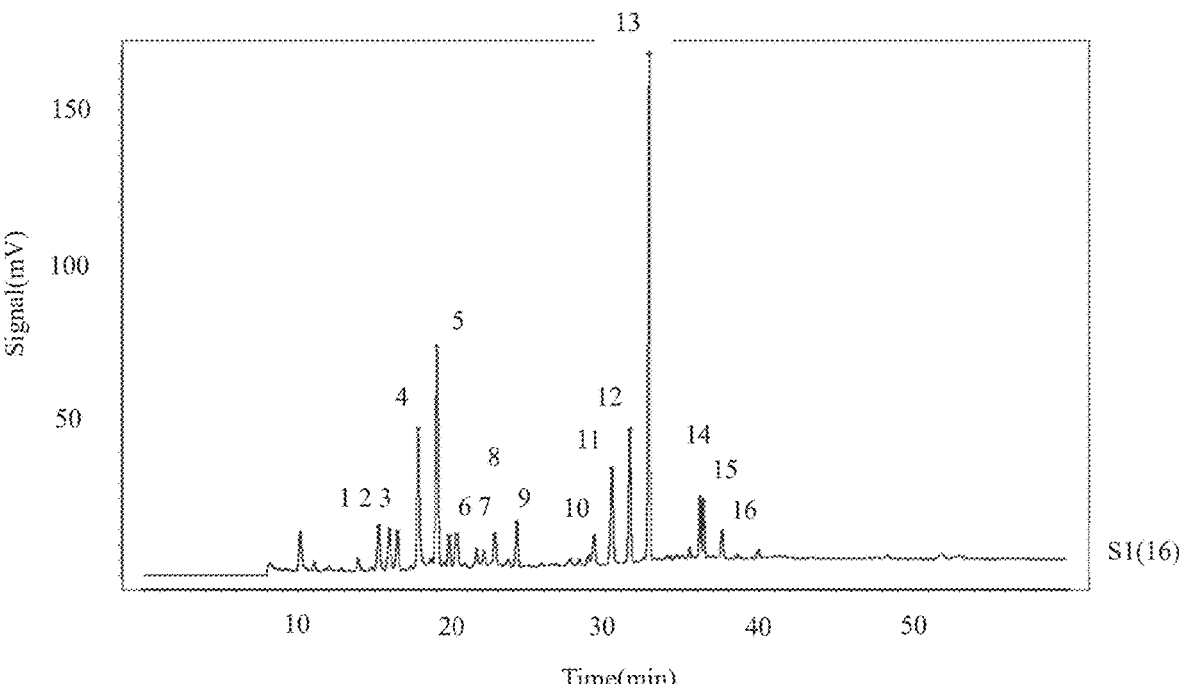
FIG. 2 shows the fingerprint chromatogram of *Poria cocos;*
Figure 3:
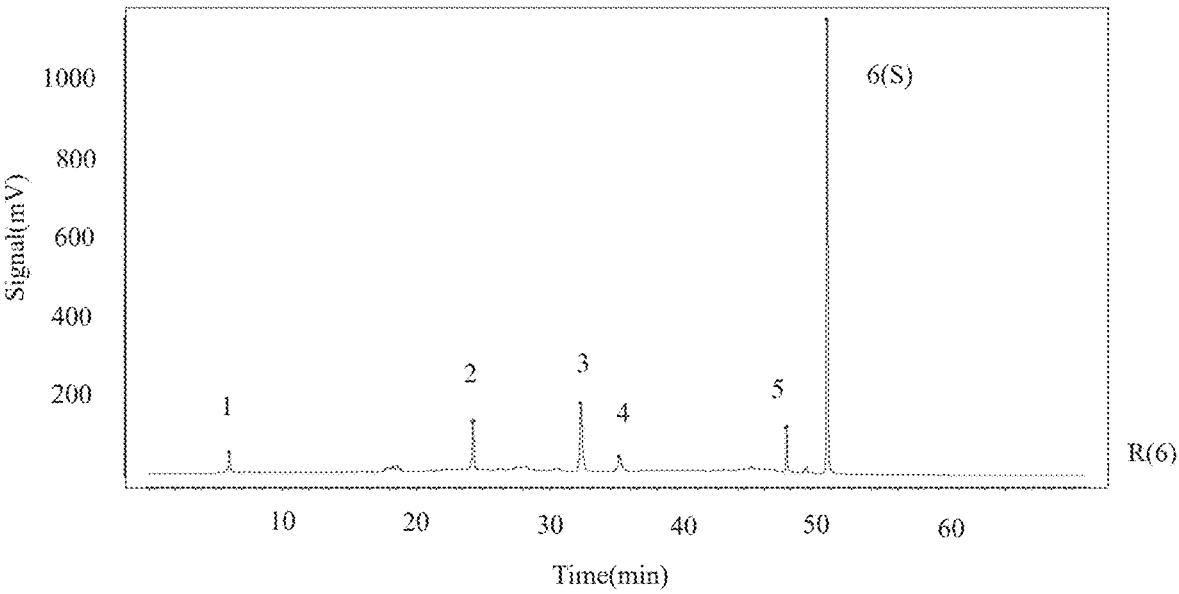
FIG. 3 shows the fingerprint chromatogram of *Cortex moutan;*
Figure 4:
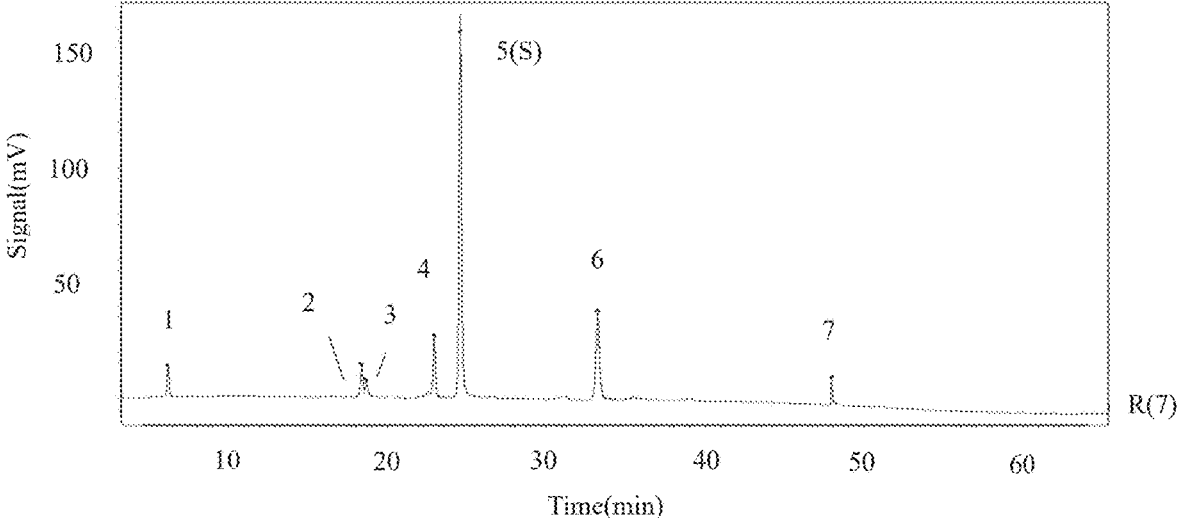
FIG. 4 shows the fingerprint chromatogram of *Radix paeoniae alba;*
Figure 5:
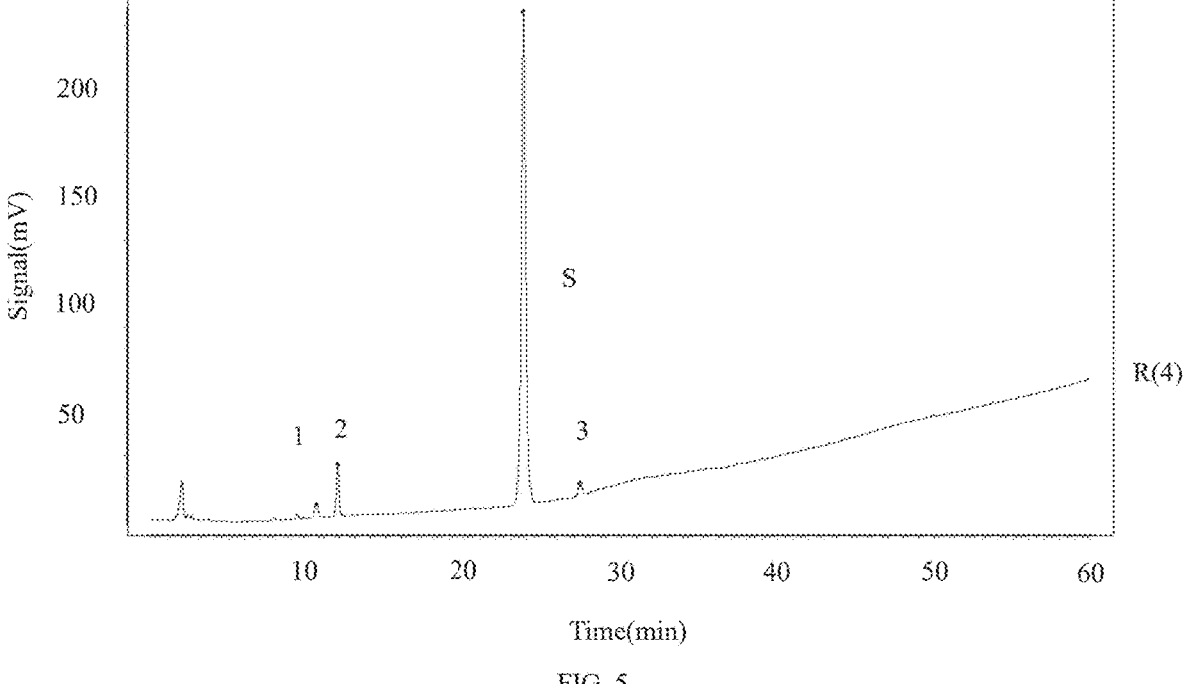
FIG. 5 shows the fingerprint chromatogram of *Semen persicae.*

As mentioned above, the present invention aims to provide a Chinese medicine composition, preparation method, use, and quality control method. The following will provide a detailed description in conjunction with the experimental examples.

It is particularly noted that similar substitutions and modifications made for the present invention are apparent to those skilled in the art and are considered to be included within the scope of the present invention. Persons skilled in the relevant art can make modifications or appropriate changes and combinations to the methods and applications described herein without departing from the scope and spirit of the present invention. Clearly, the described embodiments are only some examples of the embodiments of the present invention, rather than all embodiments.

Unless otherwise specified in the present invention, conventional conditions or conditions recommended by manufacturers are used. Reagents or instruments not specified by manufacturers are conventional products that can be obtained commercially.

In the present invention, the specific methods for determining the contents of the main components in the Chinese medicine composition are as follows:

Preparation of Sample Solution 1: Approximately 0.25 g of the sample (passed through a No. 4 sieve) is accurately weighed, extracted in parallel with 25 mL of 50% methanol as the extraction solvent, ultrasonicated for 30 minutes, cooled, weighed accurately, adjusted for weight loss with methanol, shaken well, centrifuged at 14,000 rpm for 5 minutes, and the supernatant is taken to obtain Sample Solution 1 (containing approximately 10 mg/mL of the content).

Preparation of Sample Solution 2: Approximately 0.5 g of the sample (passed through a No. 4 sieve) is accurately weighed, added precisely to 25 mL of 50% methanol, refluxed for 30 minutes, cooled to room temperature, adjusted for weight loss with methanol, shaken well, centrifuged at 14,000 rpm for 5 minutes, and the supernatant is taken as Sample Solution 2 (containing approximately 20 mg/mL of the content).

(1) the Determination of the Content of Paeoniflorin, Paeonol, Cinnamaldehyde, Cinnamic Acid, Benzoylpaeoniflorin, Oxidized Paeoniflorin, Gallic Acid, 1,2,3,4,6-O-pentagalloylglucose, p-Hydroxybenzoic Add, Ethyl Gallate, Benzoic Acid, and Amygdalin in Guizhi Fuling Capsules The methods for quantifying 12 main components (paeoniflorin, paeonol, cinnamaldehyde, cinnamic acid, benzoylpaeoniflorin, oxidized paeoniflorin, gallic acid, 1,2,3,4,6-O-pentagalloylglucose, p-hydroxybenzoic acid, ethyl gallate, benzoic acid, and amygdalin) was respectively established using HPLC-DAD and HPLC-UV-ELSD combined methods. The quantifying method was proven reliable and suitable through comprehensive evaluations including specificity, system suitability, method validation, and robustness.

Method for Amygdalin Content Determination:

Preparation of reference solution: Accurately weigh 10 mg of amygdalin into a 10 mL volumetric flask, add a small amount of 70% methanol solution, sonicate to dissolve, cool, add methanol to volume, shake well to obtain a reference stock solution. Precisely transfer 2 mL of the stock solution into a 10 mL volumetric flask, dilute with 70% methanol to volume, shake well, filter, and use the filtrate as the reference solution.

Chromatographic Conditions:

A Thermo Acclaim™ 120 $C_{18}$ (4.6×250 mm, 5 μm) column was used with mobile phase methanol (B)-water (A), gradient elution: 0-20 min (82% B), 20-25 min (82-5% B), 25-30 min (5-5% B), flow rate 1 mL·min$^{-1}$, column temperature 35° C., detection wavelength 210 nm.

Accurately inject 10 μL each of the reference solution and sample solution into the high-performance liquid chromatography system, calculate using external standard method to obtain results The determination of the content of 11 main components (paeoniflorin, paeonol, cinnamaldehyde, cinnamic acid, benzoylpaeoniflorin, oxidized paeoniflorin, gallic acid, 1,2,3,4,6-O-pentagalloylglucose, p-hydroxybenzoic acid, ethyl gallate, and benzoic acid):

Preparation of Reference Solution:

1) Preparation of Mixed Reference Solution Containing Gallic Acid, Paeoniflorin, 1,2,3,4,6-O-Penta-Galloylglucose, Ellagic Acid, and Cinnamaldehyde:

Accurately weigh 10 mg of gallic acid, 25 mg of paeoniflorin, 6 mg of 1,2,3,4,6-O-penta-O-galloylglucose, and 12 mg of paeonol, and place them together in a 25 mL volumetric flask. Accurately weigh 8 mg of cinnamaldehyde into a 10 mL volumetric flask, dissolve in methanol, dilute to volume, mix well, and precisely transfer 2 mL of this solution to the aforementioned 25 mL volumetric flask.

Dilute with 50% methanol to the mark, obtaining mixed reference solution 2. Dilute the mixed reference solution with 50% methanol to prepare 4 times diluted reference solution 3.

2) Preparation of Mixed Reference Solution Containing Oxidized Paeoniflorin, benzoic acid, benzoylpaeoniflorin, ethyl gallate, cinnamic acid, and p-Hydroxybenzoic Acid:

Accurately weigh 10 mg of oxidized paeoniflorin, 7.5 mg of benzoic acid, and 15 mg of benzoylpaeoniflorin into a 25 mL volumetric flask. Accurately weigh 15 mg of ethyl gallate, 12 mg of cinnamic acid, and 10 mg of p-hydroxybenzoic acid into a 10 mL volumetric flask, dissolve in 50% methanol and dilute to volume, mix well, and precisely transfer 2 mL of this solution to the aforementioned 25 mL volumetric flask. Dilute with 50% methanol to the mark, mix well, obtaining mixed reference solution 4. Dilute reference solution 3 with 50% methanol to prepare 4 times diluted reference solution 5.

Chromatographic Conditions:

Thermo Acclaim™ 120 C18 column (4.6×250 mm, 5 μm); Mobile phase: acetonitrile (B)-0.2% formic acid water (A); Gradient elution: 0-11 min (3-3% B), 11-15 min (3-10% B), 15-28 min (10-15% B), 28-29 min (15-16% B), 29-39 min (16-20% B), 39-45 min (20-23% B), 45-47 min (23% B), 47-51 min (23-35% B), 51-71 min (35-43% B), 71-76 min (43-95% B), 76-80 min (95% B). Flow rate: 1 mL/min; Column temperature: 30° C.; Detection wavelengths: 230 nm (paeoniflorin, benzoic acid, benzoyl paeoniflorin), 254 nm (p-hydroxybenzoic acid, oxidized paeoniflorin), 275 nm (gallic acid, ethyl gallate, 1,2,3,4,6-O-penta-galloylglucose, cinnamic acid, paeonol), 290 nm (cinnamaldehyde).

Accurately inject 10 μL each of the above reference solution and sample solution 2 into the high-performance liquid chromatography system, calculate according to external standard method to obtain the results.

(2) Determination of Polysaccharide Content a. An optimized method for polysaccharide content determination, the Anthrone-sulfuric acid colorimetric method, was established under the following optimal conditions: sulfuric acid concentration in the color reagent is 85%, measurement wavelength is 621 nm, color development time in boiling water bath is 15 minutes, the solution remains stable within 120 minutes after color development, and the standard curve shows good linearity. b. The preparation conditions of water-soluble polysaccharide sample solution were optimized through single-factor experiments, including investigation of impurity removal methods, extraction methods, and purification methods. Impurities affecting the determination of water-soluble polysaccharides, such as lipophilic small molecules, monosaccharides, oligosaccharides, and β-cyclodextrin, were removed by ultrasonic treatment with 70% ethanol. The impurity removal method was also applied to glucan standards with molecular weights of 50,000, 270,000, and 670,000 Da, confirming that the 70% ethanol treatment caused minimal polysaccharide loss. c. The preparation conditions of alkali-soluble polysaccharides were optimized through single-factor experiments, including investigation of extraction methods and purification methods. Systematic methodological validation demonstrated the feasibility of this content determination method.

Preparation of Water-Soluble Polysaccharide Sample Solution:

The sample content was thoroughly mixed, ground finely, approximately 0.5 g was accurately weighed and placed into a conical flask, then 50 mL of 70% ethanol was added. The mixture was subjected to 20 minutes of ultrasound treatment (300 W, 50 Hz), followed by centrifugation (4500 r/min, 10 min), discarding the supernatant. The precipitate was again treated with 50 mL of 70% ethanol using the same method for extraction twice. The precipitate was then mixed with 50 mL of water, reflux extracted for 60 minutes, centrifuged (4500 r/min, 10 min), the supernatant was collected, and the precipitate was treated with 50 mL of water using the same method for extraction twice. The combined supernatants were concentrated under reduced pressure to approximately 5 mL at below 60° C., with slow addition of 20 mL of ethanol while stirring. The mixture was refrigerated for 12 hours, centrifuged (4500 r/min, 10 min), the supernatant discarded, and the precipitate dissolved in hot water, transferred to a 100 mL volumetric flask, cooled, diluted with water to the mark, mixed well, filtered, and precisely measured by taking 20 mL of the filtrate and transferring it to a 100 mL volumetric flask, diluted with water to the mark, mixed well, to obtain the final solution.

Preparation of Alkali-Soluble Polysaccharide Sample Solution:

The precipitate obtained from the water-soluble polysaccharide sample solution preparation method was subjected to the following treatment: the sample content was thoroughly mixed, ground finely, approximately 0.5 g was accurately weighed and placed into a conical flask, then 50 mL of 70% ethanol was added. The mixture was subjected to 20 minutes of ultrasound treatment (300 W, 50 Hz), followed by centrifugation (4500 r/min, 10 min), discarding the supernatant. The precipitate was again treated with 50 mL of 70% ethanol using the same method for extraction twice. The precipitate was then mixed with 50 mL of water, refluxed for 60 minutes, centrifuged (4500 r/min, 10 min), the supernatant was collected, and the precipitate was treated with 50 mL of water using the same method for extraction twice. The combined supernatants were treated with 50 mL of 1 mol/L NaOH solution, subjected to 30 minutes of ultrasound treatment (300 W, 50 Hz), centrifuged (4500 r/min, 10 min), the supernatant was collected, and the precipitate was again treated with 50 mL of 1 mol/L NaOH solution using the same method for extraction twice. The combined supernatants were adjusted to a pH of approximately 5 using 5 mol/L HCl, refrigerated for 12 hours, centrifuged (4500 r/min, 10 min), the supernatant was discarded, and the precipitate was dissolved in 50 mL of 1 mol/L NaOH solution, transferred to a 100 mL volumetric flask, diluted with 1 mol/L NaOH solution to the mark, mixed well, filtered, and precisely measured by taking 2 mL of the filtrate and transferring it to a 100 mL volumetric flask, diluted with 1 mol/L NaOH solution to the mark, mixed well, to obtain the final solution.

(3) Determination of Monosaccharide and Disaccharide Content

Optimized chromatographic conditions for the determination of monosaccharide and disaccharide content were established as follows: using an XBridge Amide column (4.6 mm×250 mm, 5 μm), eluted with 0.2% triethylamine-acetonitrile (15:85) as the mobile phase, column temperature set at 45° C., flow rate at 1 mL/min, injection volume of 10 μL, and detection by refractive index detector (drift tube temperature 95° C., carrier gas flow rate 2.5 L/min). The conditions for preparation of test sample solutions were investigated and the feasibility of this method was confirmed through systematic methodological validation.

Example 1: Preparation of Traditional Chinese Medicine Composition

Raw Materials: 240 g *Cinnamomi ramulus*, 240 g *Poria cocos*, 240 g *Cortex moutan*, 240 g *Paeoniae radix alba*, 240 g *Persicae semen*, for making 1000 capsules.

Preparation Process: Among the five ingredients, *Poria cocos* (192 g) was pulverized into fine powder; *Cortex moutan* was distilled using steam to collect the distillate, extracting volatile components for later use; the herb residue, along with *Cinnamomi ramulus, Paeoniae radix alba, Persicae semen*, and the remaining *Poria cocos*, underwent dual extraction with 90% ethanol, combining the extracts and recovering ethanol until no residual taste remained, then vacuum concentrated to an appropriate volume; the herb residue was then boiled twice with water, filtered, combined the filtrates, vacuum concentrated to an appropriate volume. The above two concentrated liquids, along with finely ground *Poria cocos*, were mixed, dried, pulverized, added to an appropriate amount of dextrin, formed into granules, dried, added volatile components of *Cortex moutan*, mixed, packed in capsules, and produced into 1000 capsules (each containing 0.31 g per capsule), hence obtained.

Select medicinal materials from different origins and batches in accordance with pharmacopoeia standards. A total of 12 batches of traditional Chinese medicine compositions were prepared. The specific contents of each batch are shown in Table 1.

Table 1 Content of the primary ingredients in the 12 batches

TABLE 1

| Content of the primary ingredients in the 12 batches of Traditional Chinese Medicine composition capsules (%, grams of primary ingredients per 100 g of content) | | | | | | | |
|---|---|---|---|---|---|---|---|
| Batch active ingredients | gallic acid | p-hydroxy-benzoic acid | oxidized paeoni-florin | paeoni-florin | ethyl gallate | 1,2,3,4,6-O-penta-galloylglucose | bezoic acid |
| A | 0.650 | 0.028 | 0.159 | 1.847 | 0.039 | 0.566 | 0.107 |
| B | 0.360 | 0.050 | 0.121 | 0.091 | 0.090 | 0.155 | 0.131 |
| C | 0.519 | 0.019 | 0.124 | 1.409 | 0.029 | 0.354 | 0.083 |
| D | 0.433 | 0.054 | 0.097 | 1.235 | 0.012 | 0.294 | 0.045 |
| E | 0.357 | 0.071 | 0.072 | 1.326 | 0.157 | 0.387 | 0.079 |
| F | 0.740 | 0.011 | 0.201 | 1.991 | 0.094 | 0.702 | 0.135 |
| G | 0.855 | 0.028 | 0.216 | 1.096 | 0.017 | 0.114 | 0.040 |
| H | 0.460 | 0.045 | 0.218 | 1.145 | 0.077 | 0.356 | 0.147 |
| I | 0.314 | 0.024 | 0.195 | 1.112 | 0.082 | 0.155 | 0.181 |
| J | 0.491 | 0.068 | 0.091 | 1.147 | 0.091 | 0.186 | 0.130 |
| K | 0.356 | 0.009 | 0.108 | 1.323 | 0.046 | 0.180 | 0.051 |
| L | 0.714 | 0.046 | 0.283 | 2.256 | 0.053 | 0.632 | 0.054 |

TABLE 1-continued

| Batch active ingredients | cinna-mic acid | benzoyl-paeoni-florin | cinna-maldehyde | paeonol | amygdalin | water-soluble poly-saccharides | alkali-soluble poly-saccharides | mono-saccharides and di-saccharides |
|---|---|---|---|---|---|---|---|---|
| A | 0.040 | 0.212 | 0.139 | 0.913 | 1.492 | 3.701 | 40.206 | 9.986 |
| B | 0.070 | 0.249 | 0.027 | 1.102 | 1.001 | 3.575 | 25.149 | 7.231 |
| C | 0.042 | 0.121 | 0.355 | 1.022 | 1.435 | 3.643 | 38.231 | 12.155 |
| D | 0.062 | 0.101 | 0.045 | 1.202 | 1.351 | 3.652 | 39.414 | 11.837 |
| E | 0.037 | 0.302 | 0.340 | 0.734 | 1.333 | 3.868 | 29.311 | 7.147 |
| F | 0.021 | 0.236 | 0.511 | 0.728 | 1.114 | 1.851 | 30.198 | 15.438 |
| G | 0.072 | 0.145 | 0.140 | 0.629 | 1.131 | 3.690 | 39.992 | 19.840 |
| H | 0.055 | 0.199 | 0.536 | 0.712 | 1.136 | 4.743 | 45.847 | 23.112 |
| I | 0.025 | 0.298 | 0.542 | 0.622 | 1.402 | 3.016 | 45.020 | 12.613 |
| J | 0.025 | 0.097 | 0.434 | 0.601 | 1.671 | 1.682 | 31.671 | 17.934 |
| K | 0.077 | 0.219 | 0.521 | 0.623 | 0.813 | 2.741 | 26.155 | 7.224 |
| L | 0.061 | 0.255 | 0.533 | 0.735 | 1.323 | 3.154 | 39.913 | 10.376 |

Example 2: Experimental Study on Dysmenorrhea Rats Using 12 Batches of Traditional Chinese Medicine Combinations

1. Materials 1.1 Drugs and Reagents

Twelve batches of samples prepared according to Example 1 of the present invention; Estradiol Benzoate Injection (Lot No.: 200507, Manufacturer: Shanghai Quanyu Biotechnology (Zhumadian) Animal Pharmaceutical Co., Ltd.); Oxytocin Injection (Lot No.: 20200505, Manufacturer: Jiangxi Bolai Dapharm Co., Ltd.); 0.9% Sodium Chloride Injection (Lot No.: 2011262011, Manufacturer: Shijiazhuang Siyao Co., Ltd.); PGE2 assay kit (Catalog No.: E-EL-0034c, Wuhan Elabscience Biotechnology Co., Ltd.); PGF2α assay kit (Catalog 5 No.: E-EL-R0795c, Wuhan Elabscience Biotechnology Co., Ltd.); COX-2 assay kit (Catalog No.: H200, Nanjing Jiancheng Bioengineering Institute).

1.2 Animals

SD rats, female, SPF grade, weighing 200±10 g, purchased from the Experimental Animal Center of Suzhou University, License No.: SYXK (Su) 2014-0030. Rats were housed under standard laboratory conditions: temperature 22±2° C., humidity 60±5%, 12-hour light-dark cycle.

1.3 Instruments

Microplate Reader: Molecular Devices;

Pipettes: Eppendorf;

Centrifuge: Hunan Xiangyi Laboratory Instrument Development Co., Ltd., Model: L530.

1.4 Statistical Methods

Experimental data are presented as mean t standard deviation (S). Statistical analysis was performed using SPSS 17.0 software. Analysis of variance (ANOVA) was used for comparison, with significance set at $P<0.05$.

2 Experimental Methods 2.1 Animal Grouping and Drug Administration 140 rats were randomly divided into 14 groups: blank control group, model group, and 12 groups treated with samples from the present invention, each group containing 10 rats. Except for the blank control group, rats in other groups received subcutaneous injections of estradiol daily for 10 days (0.5 mg on days 1 and 10, and 0.2 mg on other days); starting from day 5, oral administration of sample drugs began. On day 10, rats in each group were administered oxytocin intraperitoneally (2U) 45 minutes after oral gavage with the corresponding drug, confirming the establishment of primary dysmenorrhea rat model by the presence of writhing responses. The blank control group and model group received 10 mL/kg of physiological saline daily via oral gavage.

2.2 Evaluation Indicators:

Writhing behavior was used as an indicator of dysmenorrheal pain severity in rats. After the last oral gavage of drugs, rats except those in the blank control group received intraperitoneal injections of 0.2 mL of oxytocin per rat, and the number of writhing episodes within 30 minutes and the average writhing episodes per group were observed and recorded.

After anesthetizing the rats, their backs were fixed, and uteri were exposed and dissected. The uterine body was with physiological saline 1-2 times, added with 10 times the amount of physiological saline, ground into tissue homogenate, centrifuged, and the supernatant was collected and stored at −20° C. for testing.

Rats were fasted for 12 hours before the experiment. After anesthesia, blood was drawn, centrifuged at 3000 rpm for 15 minutes, and serum was collected for analysis.

3 Experimental Results 3.1 Effects of Samples from the Present Invention on Rat Writhing Behavior Observation of writhing episodes within 30 minutes. Results are shown in Table 2.

TABLE 2

Effects of Samples from the Present Invention on writhing Episodes (±S, n = 10)

| group | dosage | number of writhing |
|---|---|---|
| blank group and model group | — | — |
| | — | 26.10 ± 6.87 |
| A | 0.36 g/kg | 16.90 ± 5.20** |
| B | 0.36 g/kg | 18.80 ± 4.66* |
| C | 0.36 g/kg | 17.20 ± 4.83** |
| D | 0.36 g/kg | 17.30 ± 4.35** |
| E | 0.36 g/kg | 18.90 ± 5.13* |
| F | 0.36 g/kg | 17.10 ± 4.11** |
| G | 0.36 g/kg | 19.00 ± 5.89* |
| H | 0.36 g/kg | 17.20 ± 4.21** |
| I | 0.36 g/kg | 19.10 ± 3.17* |
| J | 0.36 g/kg | 18.80 ± 6.78* |

TABLE 2-continued

| group | dosage | number of writing |
|---|---|---|
| | Effects of Samples from the Present Invention on writhing Episodes (±S, n = 10) | | |
| K | 0.36 g/kg | 18.80 ± 4.64* |
| L | 0.36 g/kg | 18.80 ± 6.32* |

In comparison to the model group, *P < 0.05, **P < 0.01;
In comparison to the model group, #P < 0.05, ##P < 0.01.

Table 2 shows that compared to the model group, the number of writhing responses in rats treated with various samples of the present invention significantly decreased in groups A, C, D, F, and H, with P<0.01.

3.2 Effects of the Present Invention Samples on PGF2a and PGE2 in Rat Uteri

Tissue homogenate supernatants were used for PGF2α and PGE2 quantification. Results are presented in Table 3.

TABLE 3

The impact of each group on PGF2α and PGE2 levels in the uterus of primary dysmenorrhea rat models (±S, n = 10).

| group | dosage | PGF2α(pg/mL) | PGE2(pg/mL) |
|---|---|---|---|
| blank group and | — | 129.48 ± 28.36 | 511.31 ± 9.74 |
| model group | — | 179.61 ± 33.32## | 486.33 ± 5.95## |
| A | 0.36 g/kg | 133.82 ± 11.09** | 501.30 ± 6.68** |
| B | 0.36 g/kg | 139.05 ± 25.04* | 498.24 ± 6.82* |
| C | 0.36 g/kg | 130.21 ± 11.77** | 501.46 ± 9.98** |
| D | 0.36 g/kg | 133.87 ± 17.38** | 501.28 ± 8.32** |
| E | 0.36 g/kg | 139.49 ± 22.84* | 498.76 ± 8.22* |
| F | 0.36 g/kg | 133.02 ± 10.79** | 501.40 ± 7.86** |
| G | 0.36 g/kg | 139.21 ± 40.77* | 498.31 ± 3.32* |
| H | 0.36 g/kg | 139.08 ± 19.32* | 498.36 ± 7.50* |
| I | 0.36 g/kg | 142.99 ± 42.80* | 498.81 ± 9.81* |
| J | 0.36 g/kg | 140.86 ± 32.12* | 498.07 ± 8.12* |
| K | 0.36 g/kg | 140.51 ± 21.76* | 498.51 ± 16.37* |
| L | 0.36 g/kg | 132.02 ± 30.79** | 500.82 ± 9.02** |

In comparison to the model group, *P < 0.05, **P < 0.01;
In comparison to the model group, #P < 0.05, ##P < 0.01.

The results indicate that PGF2α levels increased and PGE2 levels decreased in the model group compared to the normal group, with P<0.01. Compared to the model group, significant differences were observed in groups A, C, D, F, and L of the present invention samples, with both indicators having P values<0.01.

3.2 Effects of the Present Invention Samples on COX-2 in Rat Serum

Serum levels of COX-2 were quantified. Results are shown in Table 4.

TABLE 4

The impact of each group on COX-2 levels in the rat model of primary dysmenorrhea (±S, n = 10).

| group | dosage | COX-2(ng/mL) |
|---|---|---|
| blank group and | — | 28.48 ± 2.36 |
| model group | — | 39.61 ± 3.32## |
| A | 0.36 g/kg | 33.82 ± 1.09** |
| B | 0.36 g/kg | 35.75 ± 2.04* |
| C | 0.36 g/kg | 33.13 ± 3.77** |
| D | 0.36 g/kg | 33.87 ± 4.38** |
| E | 0.36 g/kg | 35.49 ± 2.84* |
| F | 0.36 g/kg | 32.02 ± 5.79** |
| G | 0.36 g/kg | 35.21 ± 3.77* |
| H | 0.36 g/kg | 35.78 ± 1.32* |
| I | 0.36 g/kg | 35.02 ± 3.79* |

TABLE 4-continued

The impact of each group on COX-2 levels in the rat model of primary dysmenorrhea (±S, n = 10).

| group | dosage | COX-2(ng/mL) |
|---|---|---|
| J | 0.36 g/kg | 35.16 ± 2.12* |
| K | 0.36 g/kg | 35.21 ± 2.76* |
| L | 0.36 g/kg | 33.99 ± 2.80** |

In comparison to the model group, *P < 0.05, **P < 0.01;
In comparison to the model group, #P < 0.05, ##P < 0.01.

The results indicate that COX-2 levels increased in the model group compared to the normal group, with P<0.01. Compared to the model group, significant differences were observed in groups A, C, D, F, and L of the present invention samples, with P values <0.01.

4 Conclusion

The 12 batches of samples prepared by the present invention can effectively reduce writhing responses, decrease PGF2α and COX-2 levels, and increase PGE2 levels to varying degrees. Among them, samples from groups A, C, D, and F showed significant differences in their effects on writhing responses, PGF2α, COX-2, and PGE2 levels (P<0.01). Based on these experimental results, the optimal effective content ranges for improving primary dysmenorrhea are recommended as follows: gallic acid (0.433%-0.740%), 4-hydroxybenzoic acid (0.011%-0.054%), oxidized paeoniflorin (0.097%-0.201%), paeoniflorin (1.235%-1.991%), ethyl gallate (0.012%-0.094%), 1,2,3,4,6-O-pentagalloylglucose (0.294%-0.702%), benzoic acid (0.045%-0.135%), cinnamic acid (0.021%-0.062%), benzoylpaeoniflorin (0.101%-0.236%), cinnamaldehyde (0.045%-0.511%), paeonol (0.728%-1.202%), amygdalin (1.114%-1.492%), water-soluble polysaccharides (1.851%-3.702%), alkali-soluble polysaccharides (30.198%-40.206%), and total monosaccharides and disaccharides (9.966%-15.438%).

Example 3: Establishment of Internal Control Standards

Based on the aforementioned pharmacological optimization samples, we traced the ingredient content characteristics of medicinal materials, established corresponding medicinal fingerprints as internal control standards, and refined preparation processes to ensure enhanced product quality and uniform stability.

1 Establishment of *Cinnamomi ramulus* Internal Control Standard:

Chromatographic Conditions and System Suitability: Using octadecyl silane bonded silica gel as the filler (chromatographic column: Luna C18, 4.6×250 mm, 5 μm), with 0.02% trifluoroacetic acid solution as mobile phase A and acetonitrile as mobile phase B, flow rate set at 1.0 ml/min, column temperature at 30° C., detection wavelength at 275 nm, theoretical plate number not less than 3000 calculated based on cinnamaldehyde chromatographic peaks. Elution program as per the table below:

| Time (min) | A (%) | B (%) |
|---|---|---|
| 0 | 84 | 16 |
| 15 | 74 | 26 |

-continued

| Time (min) | A (%) | B (%) |
|---|---|---|
| 30 | 67 | 33 |
| 60 | 42 | 58 |

Preparation of Reference Solution: Take an appropriate amount of cinnamaldehyde reference substance, accurately weigh, dissolve in ethanol to prepare a reference solution containing 105 μg per 1 ml.

Preparation of sample solution: Approximately 0.25 g of the product powder (passed through a No. 4 sieve), accurately weighed and placed in a conical flask, followed by precise addition of 25 ml of 70% ethanol, weighed again, reflux extracted for 40 min, cooled, weighed, added 70% ethanol to make up for evaporative loss, shaken, centrifuged, and the supernatant taken as the sample solution.

Analysis Method: Accurately pipette 10 μl each of the reference solution and sample solution into the liquid chromatograph for analysis.

Main features of this product's fingerprint profile: Should exhibit 6 characteristic peaks corresponding to the reference fingerprint, with relative retention times and relative peak areas meeting the requirements specified in Table 5. 1. Coumarin, 2. Cinnamyl alcohol, 3. Cinnamic acid, 4. 2-Methoxycinnamic

TABLE 5

| | Fingerprint Characteristics of *Cinnamomi Ramulus* | |
|---|---|---|
| Peak | Relative retention times | Relative peak areas |
| 1 | 0.594~0.726 | 0.020~0.065 |
| 2 | 0.685~0.837 | |
| 3 | 0.762~0.932 | 0.025~0.170 |
| 4 | 0.865~0.990 | |
| S | 1.000 | 1.000 |
| 5 | 1.050~1.284 | 0.045~0.153 |

2 Establishment of *Poria cocos* Internal Control Standard:

Chromatographic Conditions and System Suitability Test: Using octadecyl silane bonded silica gel as the filler (Kromasil 100-3.5-C18 (4.6×150 mm)), with 0.1% phosphoric acid aqueous solution as mobile phase A and acetonitrile as mobile phase B, flow rate set at 1.0 ml/min, column temperature at 30° C., detection wavelength at 210 nm, theoretical plate number not less than 3000 calculated based on pachymic acid chromatographic peaks. Elution program as per the table below.

| Time (min) | A (%) | B (%) |
|---|---|---|
| 0 | 50 | 50 |
| 12 | 45 | 55 |
| 16 | 40 | 60 |
| 20 | 35 | 65 |
| 24 | 30 | 70 |
| 28 | 25 | 75 |
| 32 | 15 | 85 |
| 34 | 10 | 90 |
| 60 | 10 | 90 |

Preparation of Reference Solution: Take an appropriate amount of pachymic acid reference substance, accurately weigh, dissolve in 70% methanol to prepare a reference solution containing 450 μg per 1 ml.

Preparation of sample solution: Take the product, crushed and passed through a No. 4 sieve, approximately 3 g accurately weighed and placed in a 100 ml conical bottle, add 50 ml of methanol, sonicate (500 W, 40 Hz) for 30 minutes, filter through filter paper, evaporate to dryness, dissolve in methanol to make up to 5 ml, centrifuge, and take the supernatant as the sample solution.

Analysis Method: Accurately pipette 10 μl each of the reference solution and sample solution into the liquid chromatograph for analysis.

Main features of this product's fingerprint profile: Should exhibit 16 characteristic peaks' corresponding to the reference fingerprint, with a similarity not less than 0.90 calculated using the traditional Chinese medicine chromatographic fingerprint similarity evaluation system. Simultaneously meet the requirements for relative retention time and relative peak area, as shown in Table 6.

TABLE 6

| | Fingerprint Characteristics of *Poria Cocos* | |
|---|---|---|
| Peak | Relative retention times | Relative peak areas |
| 1 | 0.371-0.557 | |
| 2 | 0.388-0.582 | |
| 3 | 0.401-0.601 | |
| 4 | 0.407-0.679 | 0.312-0.52 |
| 5 | 0.431-0.718 | 0.461-0.769 |
| 6 | 0.482-0.724 | |
| 7 | 0.495-0.743 | |
| 8 | 0.556-0.834 | |
| 9 | 0.591-0.887 | |
| 10 | 0.713-1.070 | |
| 11 | 0.742-1.112 | |
| 12 | 0.673-1.251 | 0.211-0.393 |
| 13 | 1 | 1 |
| 14 | 0.881-1.321 | |
| 15 | 0.886-1.330 | |
| 16 | 0.916-1.374 | |

Integration condition: No integration before 4 minutes.

3. Establishment of *Moutan cortex* Internal Control Standard:

Chromatographic conditions and system suitability: Using octadecylsilane-bonded silica gel as the stationary phase, Waters Symmetry C18 (4.6×250 mm); with 0.02% trifluoroacetic acid aqueous solution as mobile phase A and acetonitrile as mobile phase B; theoretical plate number not less than 4000 calculated based on the peak of reference substance (paeoniflorin). Detection wavelength: 230 nm. Elution program as per the table below:

| Time | A % | B % |
|---|---|---|
| 0→5 | 95 | 5 |
| 5→20 | 95→83 | 5→17 |
| 20→30 | 83→81 | 17→19 |
| 30→40 | 81→74 | 19→26 |
| 40→60 | 74→12 | 26→88 |
| 60→70 | 12 | 88 |

Preparation of reference solution: Take appropriate amounts of paeoniflorin, benzoylpaeoniflorin, and paeonol reference standards, precisely weigh and dissolve in 50% methanol to prepare a mixed reference solution containing 100 μg, 30 μg, and 200 μg of paeoniflorin, benzoylpaeoniflorin, and paeonol per 1 mL, respectively. Use paeonol as the reference substance.

Preparation of sample solution: Weigh approximately 0.5 g of the sample powder (passed through a No. 4 sieve), precisely weigh and place in a round-bottom flask, add 50% methanol 50 mL, determine the weight, reflux for 30 minutes in a water bath, cool, weigh again, add 50% methanol to compensate for weight loss, shake well, centrifuge (12000 rpm, 5 min), and use the supernatant as the sample solution.

Analytical method: Precisely inject 10 μl of each reference and sample solution into the liquid chromatograph for analysis.

Main features of this product's fingerprint profile: Should present 6 characteristic peaks corresponding to the reference fingerprint profile, with relative retention times and peak areas conforming to Table 7 specifications.

TABLE 7

Fingerprint Characteristics of *Moutan Cortex*

| Peak | Relative retention times | Relative peak areas |
|---|---|---|
| 1 | 0.097~0.140 | 0.035-0.210 |
| 2 | 0.388~0.557 | 0.055-0.330 |
| 3 | 0.544~0.750 | 0.240-0.750 |
| 4 | 0.592~0.813 | 0.015-0.225 |
| 5 | 0.798~0.997 | 0.040-0.160 |
| S | 1.000 | 1.000 |

4 Establishment of *Paeoniae radix alba* Internal Control Standard:

Chromatographic conditions and system suitability: Using octadecylsilane-bonded silica gel as the stationary phase, Waters Symmetry C18 (4.6×250 mm); with 0.02% trifluoroacetic acid aqueous solution as mobile phase A and acetonitrile as mobile phase B; theoretical plate number not less than 4000 calculated based on the peak of reference substance (paeoniflorin). Detection wavelength: 230 nm. Elution program as per the table below:

| Time | A % | B % |
|---|---|---|
| 0→5 | 95 | 5 |
| 5→20 | 95→83 | 5→17 |
| 20→30 | 83→81 | 17→19 |
| 30→40 | 81→74 | 19→26 |
| 40→60 | 74→12 | 26→88 |
| 60→70 | 12 | 88 |

Preparation of reference solution: Take appropriate amounts of paeoniflorin and benzoylpaeoniflorin reference standards, precisely weigh and dissolve in 50% methanol to prepare a mixed reference solution containing 100 μg and 30 μg of paeoniflorin and benzoylpaeoniflorin per 1 mL, respectively. Use paeoniflorin as the reference substance.

Preparation of sample solution: Take approximately 0.25 g of *Paeoniae radix alba* powder, precisely weigh and place in a round-bottom flask, add 50% methanol 50 mL, determine the weight, reflux for 40 minutes in a water bath, cool, weigh again, add 50% methanol to compensate for weight loss, shake well, centrifuge (12000 rpm, 5 min), and use the supernatant as the sample solution.

Analytical method: Precisely inject 10 μl of each reference and sample solution into the liquid chromatograph for analysis.

Main features of this product's fingerprint profile: Should present 7 characteristic peaks corresponding to the reference fingerprint profile, with relative retention times and peak areas conforming to Table 8 specifications.

TABLE 8

Fingerprint Characteristics of *Paeoniae Radix Alba*

| Peak | Relative retention times | Relative peak areas |
|---|---|---|
| 1 | 0.177-0.330 | 0.025-0.350 |
| 2 | 0.522-0.971 | |
| 3 | 0.532-0.988 | |
| 4 | 0.653-1.213 | 0.110-0.580 |
| 5(S) | 1 | 1 |
| 6 | 0.942-1.750 | 0.200-0.888 |
| 7 | 1.367-2.539 | 0.025-0.080 |

Content determination: Determined by high-performance liquid chromatography method (USP621). Method as per fingerprint profile.

Analytical method: Precisely inject 10 μl of each reference and sample solution into the liquid chromatograph for analysis.

5 Establishment of *Persicae semen* Internal Control Standard:

Chromatographic conditions and system suitability test: Using octadecylsilane-bonded silica gel as the stationary phase, aqueous solution as mobile phase A and methanol as mobile phase B; theoretical plate number not less than 3000 calculated based on the peak of reference substance (amygdalin). Detection wavelength: 218 nm. Elution program as per the table below:

| Time min | A % | B % |
|---|---|---|
| 0 | 90 | 10 |
| 10 | 85 | 15 |
| 20 | 82 | 18 |
| 40 | 60 | 40 |
| 60 | 35 | 65 |

Preparation of reference solution: Take an appropriate amount of amygdalin reference standard, accurately weigh, dissolve in 70% methanol to prepare a solution containing 600 μg per 1 mL, using amygdalin solution as the reference substance.

Preparation of sample solution: Take an appropriate amount of the sample, pass through a No. 2 sieve, mix thoroughly, take approximately 0.5 g, accurately weigh, place in a 50 mL round-bottom flask, add 25 mL of 70% methanol, accurately weigh, reflux for 30 minutes, cool, weigh again, add 70% methanol to compensate for weight loss, shake well, centrifuge to obtain the supernatant as the sample solution.

Analytical method: Precisely pipette 10 μl of each reference and sample solution into the liquid chromatograph for analysis.

Main features of this product's fingerprint profile: Should present 4 characteristic peaks corresponding to the reference fingerprint profile, with relative retention times and peak areas conforming to Table 9 specifications.

TABLE 9

Fingerprint Characteristics of *Persicae Semen*

| Peak | Relative retention times | Relative peak areas |
|---|---|---|
| 1 | 0.383~0.542 | 0.010-0.050 |
| 2 | 0.433~0.665 | 0.025-0.110 |

TABLE 9-continued

Fingerprint Characteristics of *Persicae Semen*

| Peak | Relative retention times | Relative peak areas |
|------|--------------------------|---------------------|
| S | 1 | 1 |
| 3 | 1.033~1.321 | / |

6 Validation experiments: Select herbs from different origins and batches, verify compliance with the above internal control standards. Prepare and analyze 10 batches of herbal combinations using the aforementioned standards, raw materials, and procedures. Determine the content of relevant components, with results as follows:

Content (%) of main components in 10 batches of herbal capsule contents:

| Batch active ingredients | gallic acid | p-hydroxy-benzoic acid | oxidized paeoniflorin | paeoni-florin | ethyl gallate | 1,2,3,4,6-O-penta-galloylglucose | bezoic acid |
|---|---|---|---|---|---|---|---|
| 1 | 0.650 | 0.046 | 0.159 | 1.841 | 0.079 | 0.616 | 0.107 |
| 2 | 0.490 | 0.020 | 0.121 | 1.391 | 0.027 | 0.355 | 0.065 |
| 3 | 0.519 | 0.039 | 0.134 | 1.409 | 0.039 | 0.354 | 0.083 |
| 4 | 0.483 | 0.031 | 0.118 | 1.335 | 0.034 | 0.387 | 0.055 |
| 5 | 0.557 | 0.034 | 0.138 | 1.321 | 0.047 | 0.504 | 0.079 |
| 6 | 0.710 | 0.049 | 0.186 | 1.891 | 0.084 | 0.634 | 0.125 |
| 7 | 0.655 | 0.042 | 0.172 | 1.696 | 0.077 | 0.576 | 0.080 |
| 8 | 0.460 | 0.030 | 0.109 | 1.342 | 0.027 | 0.355 | 0.057 |
| 9 | 0.514 | 0.037 | 0.145 | 1.591 | 0.082 | 0.486 | 0.081 |
| 10 | 0.491 | 0.033 | 0.121 | 1.281 | 0.029 | 0.351 | 0.051 |

| Batch active ingredients | cinnamic acid | benzoyl-paeoniflorin | cinna-maldehyde | paeonol | amygdalin | water-soluble poly-saccharides | alkali-soluble poly-saccharides | mono-saccharides and di-saccharides |
|---|---|---|---|---|---|---|---|---|
| 1 | 0.040 | 0.212 | 0.139 | 0.913 | 1.395 | 2.701 | 38.206 | 12.966 |
| 2 | 0.037 | 0.149 | 0.097 | 1.102 | 1.201 | 2.375 | 35.149 | 11.231 |
| 3 | 0.042 | 0.201 | 0.355 | 1.026 | 1.315 | 2.643 | 38.231 | 12.155 |
| 4 | 0.052 | 0.135 | 0.095 | 1.142 | 1.251 | 3.272 | 39.414 | 14.637 |
| 5 | 0.037 | 0.156 | 0.134 | 0.834 | 1.333 | 2.258 | 34.311 | 10.947 |
| 6 | 0.042 | 0.202 | 0.411 | 0.858 | 1.424 | 1.985 | 31.965 | 10.438 |
| 7 | 0.040 | 0.179 | 0.140 | 0.829 | 1.341 | 3.490 | 39.192 | 14.840 |
| 8 | 0.055 | 0.126 | 0.236 | 0.922 | 1.204 | 2.743 | 37.847 | 13.112 |
| 9 | 0.035 | 0.173 | 0.242 | 0.982 | 1.371 | 3.316 | 39.020 | 13.813 |
| 10 | 0.043 | 0.133 | 0.344 | 0.961 | 1.281 | 2.682 | 37.674 | 12.934 |

The results show that the content of active ingredients in the herbal combinations prepared according to the above internal control standards and methods is stable, indicating consistent therapeutic efficacy.

The above serves as an illustrative example of the implementation of the invention. It should be noted that for those skilled in the art, various improvements and modifications can be made without departing from the principles of the invention, which should also be considered within the scope of protection of the invention.

What is claimed is:

1. A medicine composition, in a dosage form and therapeutically-effective amounts for the treatment or improvement of dysmenorrhea or a condition characterized thereby, the composition comprising active ingredients derived from *Cinnamomi ramulus, Poria cocos, Moutan cortex, Persicae semen*, and *Paeoniae radix alba*, quantified in mass percentages, the active ingredients comprising, by weight of the medicine composition:

0.433-0.740 parts by weight of gallic acid, 0.011-0.054 parts by weight of p-hydroxybenzoic acid, 0.097-0.201 parts by weight of oxidized paeoniflorin, 1.235-1.991 parts by weight of paeoniflorin, 0.012-0.094 parts by weight of ethyl gallate, 0.294-0.702 parts by weight of 1,2,3,4,6-O-penta-galloyl-glucose, 0.045-0.135 parts by weight of benzoic acid, 0.021-0.062 parts by weight of cinnamic acid, 0.101-0.236 parts by weight of benzoylpaeoniflorin, 0.045-0.511 parts by weight of cinnamaldehyde, 0.728-1.202 parts by weight of paeonol, 1.114-1.492 parts by weight of amygdalin, 1.851-3.702 parts by weight of water-soluble polysaccharides, 30.198-40.206 parts by weight of alkali-soluble polysaccharides, and 9.966-15.438 parts by weight of monosaccharides and disaccharides.

2. The medicine composition according to claim 1, wherein the dosage form is selected from the group consisting of a tablet, capsule, pill, granule, powder, and pellet.

3. A medicine composition according to claim 1, wherein composition is obtainable by a method comprising:

weighing raw medicinal materials including *Cinnamomi ramulus, Poria cocos, Moutan cortex, Persicae semen*, and *Paeoniae radix alba;* wherein 80% of the amount of *Poria cocos* is powdered; and wherein the *Moutan cortex* is steam-distilled with water vapor to collect the distillate, from which volatile components are separated and set aside; wherein the residue thereof, along with the *Cinnamomi ramulus, Paeoniae radix alba, Persicae semen* and the remaining 20% of the amount *Poria cocos*, is extracted twice with 90% ethanol and the ethanolic extracts combined;

wherein ethanol is removed from the combined extracts by evaporation, and the resulting residue is further extracted twice with water and the aqueous filtrates combined, concentrated under reduced pressure, and mixed with finely powdered *Poria cocos* and the volatile components of *Moutan cortex*.

4. The medicine composition according to claim 3, wherein, the HPLC chromatogram fingerprint characteristics of the raw materials comprise:

(A) *Cinnamomi ramulus* having the following characteristics:

| Peak | Relative Retention Times | Relative Peak Areas |
|------|--------------------------|---------------------|
| 1 | 0.594-0.726 | 0.020-0.065 |
| 2 | 0.685-0.837 | |
| 3 | 0.762-0.932 | 0.025-0.170 |
| 4 | 0.865-0.990 | |
| S | 1.000 | 1.000 |
| 5 | 1.050-1.284 | 0.045-0.153 |

(B) *Poria cocos* having the following characteristics:

| Peak | Relative Retention Times | Relative Peak Areas |
|------|--------------------------|---------------------|
| 1 | 0.371-0.557 | |
| 2 | 0.388-0.582 | |
| 3 | 0.401-0.601 | |
| 4 | 0.407-0.679 | 0.312-0.52 |
| 5 | 0.431-0.718 | 0.461-0.769 |
| 6 | 0.482-0.724 | |
| 7 | 0.495-0.743 | |
| 8 | 0.556-0.834 | |
| 9 | 0.591-0.887 | |
| 10 | 0.713-1.070 | |
| 11 | 0.742-1.112 | |
| 12 | 0.673-1.251 | 0.211-0.393 |
| 13 | 1.000 | 1.000 |
| 14 | 0.881-1.321 | |
| 15 | 0.886-1.330 | |
| 16 | 0.916-1.374 | |

(C) *Moutan cortex* having the following characteristics:

| Peak | Relative Retention Times | Relative Peak Areas |
|------|--------------------------|---------------------|
| 1 | 0.097-0.140 | 0.035-0.210 |
| 2 | 0.388-0.557 | 0.055-0.330 |
| 3 | 0.544-0.750 | 0.240-0.750 |
| 4 | 0.592-0.813 | 0.015-0.225 |
| 5 | 0.798-0.997 | 0.040-0.160 |
| S | 1.000 | 1.000 |

(D) *Paeoniae radix alba* having the following characteristics:

| Peak | Relative Retention Times | Relative Peak Areas |
|------|--------------------------|---------------------|
| 1 | 0.177-0.330 | 0.025-0.350 |
| 2 | 0.522-0.971 | |
| 3 | 0.532-0.988 | |
| 4 | 0.653-1.213 | 0.110-0.580 |
| 5(S) | 1.000 | 1.000 |
| 6 | 0.942-1.750 | 0.200-0.888 |
| 7 | 1.367-2.539 | 0.025-0.080 | and (E) *Persicae semen* having the following characteristics:

| Peak | Relative Retention Times | Relative Peak Areas |
|------|--------------------------|---------------------|
| 1 | 0.383-0.542 | 0.010-0.050 |
| 2 | 0.433-0.665 | 0.025-0.110 |

-continued

| Peak | Relative Retention Times | Relative Peak Areas |
|------|--------------------------|---------------------|
| S | 1.000 | 1.000 |
| 3 | 1.033-1.321. | |

5. A method of preparing the medicine composition according to claim 1, wherein the method comprises the following steps:

weighing raw medicinal materials including *Cinnamomi ramulus, Poria cocos, Moutan cortex, Persicae semen*, and *Paeoniae radix alba*, to obtain said raw materials in a 1:1:1:1:1 ratio by weight;

obtaining (a) a first portion of the *P. cocos* consisting of 80% of the *P. cocos* raw material, wherein the first portion is in the form of a powder and (b) a second portion of the *P. cocos* consisting of 20% of the *P. cocos* raw material;

obtaining the *Moutan cortex*, wherein the *M. cortex* is obtained by steam-distilling the raw material with water vapor to collect the distillate thereof, separating and setting aside volatile components from the distillate, and thereby obtaining a residual *M. cortex* distillate;

mixing the residual *M. cortex* distillate, along with the *C. ramulus, P. radix alba, P. semen* and the second portion of *P. cocos*;

extracting the mixture with ethanolic and aqueous extractions, wherein the ethanolic extraction comprises extracting twice with 90% ethanol, combining the ethanolic extracts, and evaporating the ethanol therefrom to obtain an extraction residue, and wherein the aqueous extraction comprises further extracting said extraction residue twice with water, and combining and concentrating under reduced pressure the filtrates thereof, and mixing the concentrated filtrate with the first portion of *P. cocos* and the volatile components of *M. cortex*, thereby obtaining said medicine composition.

6. The method according to claim 5, wherein the step of mixing the concentrated filtrate with the first portion of *P. cocos* and the volatile components of *M. cortex*, comprises:

mixing: (i) the first portion of *P. cocos*, wherein the portion is finely-powdered, with (ii) the concentrated filtrate, and drying to obtain a dry paste therefrom and then to the dry paste: granulating with dextrin, drying, and encapsulating with the volatile components of *M. cortex*, thereby obtaining said medicine composition in a capsule dosage form.

7. A method for preparing the medicine composition according to claim 1, wherein the method comprises the following steps:

weighing raw medicinal materials including *Cinnamomi ramulus, Poria cocos, Moutan cortex, Persicae semen*, and *Paeoniae radix alba* to obtain said raw materials in a 1:1:1:1:1 ratio by weight;

grinding into coarse powder and mixing uniformly the *Cinnamomi ramulus, Persicae semen, Paeoniae radix alba, Moutan cortex*, and a first half of the amount of *Poria cocos* to the uniform mixture, adding 90% ethanol in an amount of 3 times the amount of the medicinal materials, and therewith soaking for 0.5 hours, refluxing for 1 hour, and then filtering to obtain a first filtrate and residue;

refluxing the residue with 90% ethanol at 3 times the amount of raw medicinal materials, and then filtering to obtain a second filtrate and residue, and combining the first and second filtrates to obtain an ethanolic extract; refluxing the second residue with 5 times the amount of water for 0.5 h, and then filtering to obtain a third filtrate and residue;

refluxing the third residue with 5 times the amount of water for 0.5 h, and then filtering to obtain a fourth filtrate and residue;

combining the third and fourth filtrates to obtain an aqueous extract, and discarding the residue, concentrating the ethanolic extract and aqueous extract separately under reduced pressure, comprising recovering the ethanolic extract until no alcohol odor remains, thereby obtaining concentrated solutions of each;

combining the two concentrated solutions to obtain a brown paste; mixing the paste with the remaining second half of the *Poria cocos* wherein the *P. cocos* is finely powdered; and drying and pulverizing the paste to obtain the medicine composition in the form of a dry paste powder.

8. A method for treating a condition using the medicine composition according to claim 1, the method comprising administering a therapeutically-effective amount of the medicine composition to a subject sufficient to treat or improve a condition, wherein the condition is selected from dysmenorrhea or a condition characterized thereby.

\* \* \* \* \*

22